United States Patent
Strongin et al.

(10) Patent No.: US 6,534,316 B2
(45) Date of Patent: Mar. 18, 2003

(54) COLORIMETRIC AND FLUORIMETRIC ANALYSIS OF CARBOHYDRATES

(75) Inventors: Robert M. Strongin, Baton Rouge, LA (US); Larry Allen Cabell, Houston, TX (US); Nadia St. Luce, Baton Rouge, LA (US); Patrick T. Lewis, Chattanooga, TN (US); Ming He, Baton Rouge, LA (US); Jorge O. Escobedo Cordova, Baton Rouge, LA (US); Claude Joseph Davis, Wheeling, IL (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 16 days.

(21) Appl. No.: 09/778,158

(22) Filed: Feb. 5, 2001

(65) Prior Publication Data

US 2002/0142475 A1 Oct. 3, 2002

(51) Int. Cl.[7] ................................................ G01N 33/00
(52) U.S. Cl. ............................. 436/94; 436/93; 436/95; 436/164; 436/166; 436/169; 436/172; 568/765
(58) Field of Search ............................... 436/93, 94, 95, 436/164, 166, 169, 172; 536/1.11, 123.1, 123.13; 568/765

(56) References Cited

U.S. PATENT DOCUMENTS 5,208,148 A * 5/1993 Haugland et al. ............. 435/14

OTHER PUBLICATIONS

Rogers et al. "Rapid spectrophotofluorometric method for determining nanogram quantities of carbohydrates", Anal. Chem. (1966), 38(13), 1851–3 (Abstract).*
Chaplin, M., "Monosaccharides," pp. 1–41 in M. Chaplin et al. (Eds.), Carbohydrate Analysis. A Practical Approach (Oxford University Press 1994).
Davis, C. et al., "Simple and Rapid Visual Sensing of Saccharides," Organic Letters, vol. 1, pp. 331–334 (1999).
James, T. et al., "Saccharide Sensing with Molecular Receptors Based on Boronic Acid," Angew. Chem. Int. Ed. Engl., vol. 35, pp. 1910–1922 (1996).
Kennedy, J. et al., "Oligosaccharides," pp. 43–67 in M. Chaplin et al. (Eds.), Carbohydrate Analysis. A Practical Approach (Oxford University Press 1994).
Koumoto, K. et al., "Design of a Visualized Sugar Sensing System Utilizing a Boronic Acid–azopyridine Interaction," Supramolecular Chemistry, vol. 9, pp. 203 ff (1998).
Koumoto, K. et al., "Colorimetric Sugar Sensing Method Useful in 'Neutral' Aqueous Media," Chem. Lett., pp. 856–857 (2000).
Lewis, P. et al., "Tetraarylboronic Acid Resorcinarene Stereoisomers. Versatile New Substrates for Divergent Polyfunctionalization and Molecular Recognition," J. Org. Chem., vol. 62, pp. 6110–6111 (1997).
Lewis, P. et al., "Visual Sensing of Saccharides Promoted by Resorcinol Condensation Products," Organic Letters, vol. 2, pp. 589–592 (2000).
Mattoo, R. et al., "Quantitative determination of sialic acid in the monosialoganglioside, GM1, by the thiobarbituric acid method," Anal. Biochem., vol. 246, pp. 30–33 (1997).
Sobenin, I. et al., "Optimization of the assay for sialic acid determination in low density lipoprotein," J. Lipid Res., vol. 39, pp. 2293–2299 (1998).
R. Strongin, "Biomolecule Color Sensing," unpublished manuscript (2000).
Ward, C. et al., "A Molecular Colour Sensor for Monosaccharides," J. Chem. Soc., Chem. Commun., pp. 229–230 (2000).

* cited by examiner

Primary Examiner—Jill Warden
Assistant Examiner—Yelena Gakh
(74) Attorney, Agent, or Firm—John H. Runnels

(57) ABSTRACT

Methods are disclosed for the simple, rapid, and selective colorimetric detection of carbohydrates, including fructose, glucose, sialic acid, and oligosaccharides. There is no need for any prior hydrolysis or other chemical modification or of the analytes. Resorcinarenes, xanthene dyes, and related compounds, formally produced by the reaction of 2 equivalents of resorcinol and a suitable electrophilic condensation partner, are used as chromophores or fluorophores for the detection of sugars and other carbohydrates.

28 Claims, No Drawings

COLORIMETRIC AND FLUORIMETRIC ANALYSIS OF CARBOHYDRATES

This invention pertains to the detection of carbohydrates, and to synthetic compounds that exhibit colorimetric or fluorimetric responses in the presence of sugars and other carbohydrates.

Several efficient methods are available for analyzing amino acids or nucleic acids. By contrast, no single method is available that is suitable for the quantitative or qualitative analysis of saccharides generally. The high degree of structural similarity between different sugars hinders their selective detection. The direct visible detection of sugars is especially challenging, since unmodified saccharides generally do not absorb light in the visible region. See generally M. Chaplin, "Monosaccharides," pp. 1–41 in M. Chaplin et al. (Eds.), Carbohydrate Analysis. A Practical Approach (Oxford University Press 1994); and J. Kennedy et al., "Oligosaccharides," pp. 43–67 in M. Chaplin et al. (Eds.), Carbohydrate Analysis. A Practical Approach (Oxford University Press 1994).

Color assays for saccharides have been reported, including those based on certain synthetic molecules and those based on certain enzymes. Color assays based on synthetic molecules are typically less expensive than enzymatic methods, and their reagents are generally more resistant to degradation. Enzymatic assays can offer greater specificity than the non-enzymatic color tests, but they are generally more expensive, and their reagents are less stable. The inherently unstable enzymes must be protected from extreme conditions during manufacture, storage, and use. An ideal detection technique for sugars would be highly specific, and would employ relatively inexpensive and stable, non-enzymatic reagents.

Problem 1. Selective Visible Detection of Fructose.

Fructose is a nearly ubiquitous component of nutrient products. Non-enzymatic glycosidation products form more rapidly in vivo from fructose than from glucose. Fructose is absorbed by the gastrointestinal tract more slowly than is glucose, and does not require insulin for entry into the liver. These features make it appealing for use by diabetics. However, fructose has a higher tendency to be converted to fat rather than glycogen, thereby producing elevated blood triglyceride levels. High D-fructose intake has been implicated in the pathogenesis of hypertriglyceridaemia, atherosclerosis, and insulin resistance.

A glucose-fructose syrup is used in many food and beverage products. The worldwide production of high fructose syrup (HFS) is currently about $8 \times 10^9$ kg per year.

Carbohydrates comprise >98% of the soluble solids in fruit juices such as apple juice and orange juice. For example, fructose and glucose are the main carbohydrate constituents of apple juice, in a ratio greater than 2 fructose: 1 glucose.

There is an unfilled need for a simple and rapid color test that is highly specific for fructose, even in the presence of other monosaccharides such as glucose, a color test that does not require the corrosive, expensive, or degradable materials that are the basis of current monosaccharide color assays. Such a test could be of global benefit to industry and biomedicine.

The selective determination of fructose in plasma is especially challenging. Glucose is typically present in plasma in 100-fold excess of fructose. The determination of fructose levels in human plasma cannot currently be performed reliably, largely due to the "excess" glucose levels. Measured levels of plasma fructose thus vary greatly among laboratories, and vary by the technique employed.

The AOAC (formerly the Association of Official Analytical Chemists) official methods for the analysis of fructose rely principally on gas chromatography (GC), and high performance liquid chromatography (HPLC) with refractive index detection. The gas chromatography analysis typically employs a prior derivatization of the sugars (e.g., methylation or trimethylsilation). Refractive index detection in HPLC is subject to significant cross-sensitivity to other, non-specific sugars and biomolecules. More recently, an electrochemical method, pulsed amperometric detection (PAD), has gained widespread use for monosaccharide detection in conjunction with HPLC; however, PAD is limited by the need to operate at high pH which, in turn, limits the choice of solvents and conditions. Mass detectors can be very useful when coupled to HPLC or GC systems; however, mass spectroscopy adds a further degree of complication and expense to the analysis. Simple reducing sugar assays can be used in automated post-column detection systems for monosaccharides including fructose; however, they also require harsh reagents and conditions. Enzyme-based assays have also been used for specific fructose determination; however, enzymes are expensive and are readily degradable.

Recent studies have described the visual color sensing of monosaccharides, including fructose, by boronic acid-appended dyes. These techniques rely on sensing changes in color promoted either by the perturbation of an aggregation-disaggregation equilibrium (i.e, the addition of saccharides promotes the disaggregation of the boronic acid-functionalized dye); or by the perturbation by a sugar of the interaction of the boronic acid with a neighboring amine (attached to an azo dye), producing charge transfer effects. See, e.g., T. James et al., "Saccharide Sensing with Molecular Receptors Based on Boronic Acid," Angew. Chem. Int Ed. Engl., vol. 35, pp. 1910–1922 (1996); K. Koumoto et al., "Design of a Visualized Sugar Sensing System Utilizing a Boronic Acid-azopyridine Interaction," Supramolecular Chemistry, vol. 9, pp. 203 ff(1998); and K. Koumoto et al., "Colorimetric Sugar Sensing Method Useful in 'Neutral' Aqueous Media," Chem. Lett., pp. 856–857 (2000).

In one modification, an optical wavelength shift has been observed following the binding of glucose in aqueous methanol; however, this modified system operates only at high pH (>12). See C. Ward et al., "A Molecular Colour Sensor for Monosaccharides," J. Chem. Soc., Chem. Commun., pp. 229–230 (2000).

Our research group has previously reported certain boronic acid-containing resorcinol condensation products (compounds 1 and 2 below), and their use in the non-selective color detection of sugars. See P. Lewis et al., "Tetraarylboronic Acid Resorcinarene Stereoisomers. Versatile New Substrates for Divergent Polyfunctionalization and Molecular Recognition," J. Org. Chem., vol. 62, pp. 6110–6111 (1997); and C. Davis et al., "Simple and Rapid Visual Sensing of Saccharides," Organic Letters, vol. 1, pp. 331–334 (1999). Although different colors were observed for reactions with different sugars in the latter paper, the method of this paper is considered non-selective in the sense that it does not allow the selective detection of a single sugar of interest when it occurs in a background of other sugars.

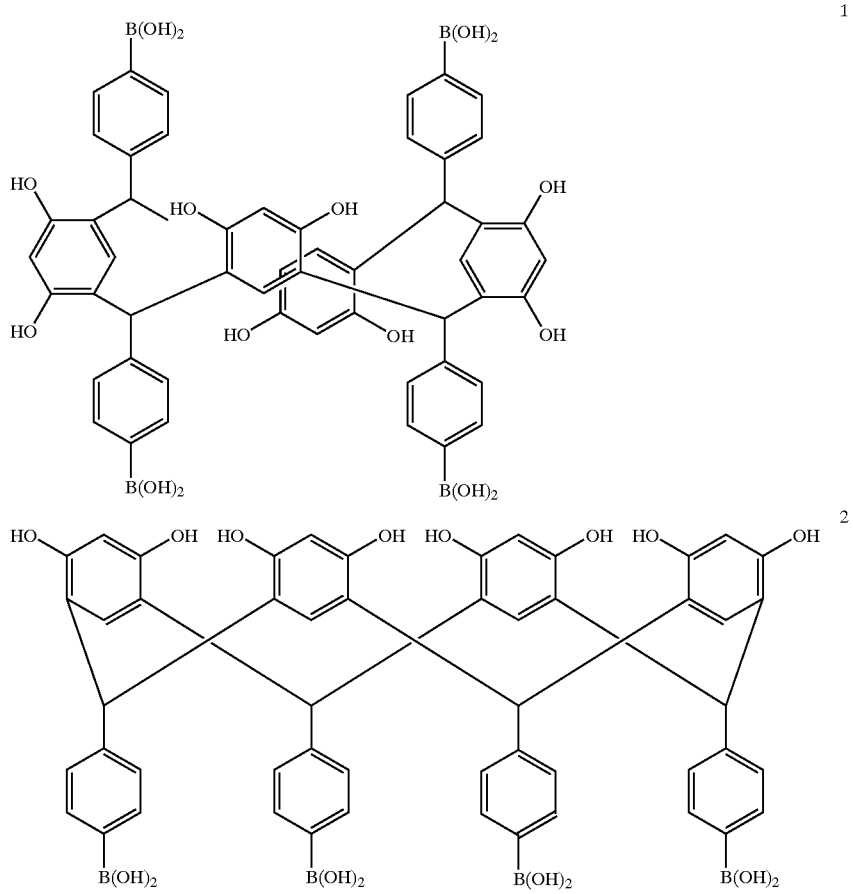

Problem 2. Mild and Selective Detection of Sialic Acid.

Sialic acids are common components of glycoproteins, glycopeptides and glycolipids. Sialic acids play a role in cell-to-cell communication in humans and other animals, and have been implicated in increased virulence in some bacteria. Imbalances in sialic acid levels can alter cell adhesion, which may have an effect in certain cancers and in some types of graft rejection. An increase in either soluble or cellular sialic acid levels can be a diagnostic marker for cancer. The function of sialic acids is incompletely understood. They appear to act as amphiphilic donors of negative charge to the cell surface. Improved methods for analyzing sialic acids would greatly aid in the elucidation of their biochemistry and in the detection of certain cancers.

The most commonly used assays for sialic acid are probably the Warren assay and the Svennerholm color test. These assays require high temperatures, harsh and toxic reagents, and are subject to interference from other carbohydrates. Free sialic acids for the Warren and Svennerholm assay are obtained by either acidic or enzymatic (e.g., neuraminidase-promoted) hydrolysis. Acidic hydrolysis leads to the liberation of both sialic acids and L-fucose. Unfortunately, L-fucose interferes with the absorbance for sialic acid measured in the Warren assay. Additionally, fructose interferes with both the Warren and Svennerholm assays. See, e.g., I. Sobenin et al., "Optimization of the assay for sialic acid determination in low density lipoprotein," *J. Lipid Res.*, vol. 39, pp. 2293–2299 (1998); and R. Mattoo et al., "Quantitative determination of sialic acid in the monosialoganglioside, $GM_1$, by the thiobarbituric acid method," *Anal. Biochem.*, vol. 246, pp. 30–33 (1997).

The Warren assay typically uses a harsh periodate oxidation of sialic acid, treatment with phosphoric acid, treatment with toxic sodium arsenite, and the use of corrosive sulfuric acid. Also required are further treatment with thiobarbituric acid and redistilled cyclohexanone, and 15 min heating at 100° C.

There is an unfilled need for an assay for sialic acid that does not require harsh reagents or harsh conditions, and that is not subject to substantial interference from fructose, fucose, and other neutral carbohydrates.

Problem 3. Color Detection of Oligosaccharides.

Glycobiology has attracted much recent attention due, in large part, to the therapeutic potential of many oligosaccharides. Many different oligosaccharides naturally occur in glycoproteins and in cell surfaces. The problems of analyzing monosaccharides are compounded with oligosaccharides due to the tremendous variety of linear and branched oligosaccharides.

A leading author has observed, "Detection of oligosaccharides eluting from HPLC columns is the biggest challenge and weakest link in the analysis of oligosaccharides." J. Kennedy et al. (1994), p. 62. There is an unfilled need for a simple method for the visible detection of oligosaccharides. There are currently no useful direct color tests for higher molecular weight oligosaccharides. Refractive index detectors are typically used to detect oligosaccharides in HPLC analyses, but refractive index detection is highly sensitive to the temperature used and the nature of the mobile phase employed, and refractive index detection is also susceptible to non-specific cross-reactivity. UV detection at wavelengths below 210 nm is another option, but UV detection limits solvent choice and requires expensive ultra-pure solvents to reduce interferences. Electrochemical detection by pulsed amperometric detection (PAD) requires high pH conditions. Mass spectrometry, coupled with chromatographic separations, requires highly specialized and expensive equipment. Aromatic or heterocyclic substituents have been used as chromogenic labels to facilitate UV detection of oligosaccharides. Radioactive labeling has also been used, but has the obvious disadvantage that it requires the handling of radioactive substances.

Classical color tests for monosaccharides fail to reliably detect oligosaccharides containing more than three monosaccharide residues. The color response in a classical color test is typically a function of the molar concentration of oligosaccharide, not its concentration by weight. For example, the response of maltohexaose has been reported to be about 18% of that for the same concentration by weight of glucose (maltohexaose is comprised of six glucose units). J. Kennedy et al. (1994), p. 46.

We have discovered novel methods for the simple, rapid, and selective colorimetric detection of carbohydrates, including fructose, glucose, sialic acid, and oligosaccharides. There is no need for any prior hydrolysis or other chemical modification or of the analytes. Resorcinarenes, xanthene dyes, and related compounds, formally produced by the reaction of 2 equivalents of resorcinol and a suitable electrophilic condensation partner, are used as chromophores or fluorophores for the detection of sugars and other carbohydrates.

The receptors of the novel method require neither azo moieties nor amine moieties, and they do not tend to aggregate in solution. High pH is not required.

Fields in which the present invention should prove useful include medical diagnostics, quality control, the fermentation industry, breweries, the food industry. in all these fields, the detection of saccharides is of great importance.

The novel method for the detection of fructose provides a simple, rapid procedure using relatively inexpensive and stable synthetic reagents. The method affords the highest selectivity of any known synthetic receptor for fructose in the presence of glucose at room temperature. For example, in the presence of 100 equivalents of glucose the absorbance of the novel chemosensor/fructose complex at 464 nm has been seen to be virtually unchanged as compared to that of fructose alone (in the absence of glucose). By contrast, absorbance at 535 nm changes as a function of glucose concentration. Thus monitoring absorbance at two wavelengths allows for the simultaneous determination of both fructose and glucose levels. We have observed that the method is also selective for fructose in the presence of other neutral carbohydrates, for example, α-lactose monohydrate, maltose monohydrate, D-(+)-xylose, D-(+)-glucose, and sucrose.

No synthetic receptor for detecting fructose at visual wavelengths has been previously reported that is not subject to significant interference from other commonly occurring carbohydrates, such as glucose. The current invention achieves an unprecedented degree of selectivity for fructose using a method that is easy to implement, and that does not require harsh reaction conditions.

The novel method for detecting sialic acid was not adversely affected by the presence of other carbohydrates, for example, D-(-)-fructose, L-fucose, D-(+)-glucose, and D-glucosamine hydrochloride; nor was the method adversely affected by the presence of amino acids, for example, L-cysteine. The sialic acid analysis is fast and simple, and can be successfully used at mild, room-temperature conditions using non-corrosive reagents at neutral or near-neutral pH.

In the presence of compounds 4 and 5, no significant relative decrease in visible absorbance intensities were observed for glucose and the maltodextrin oligomers, a prototypical series of carbohydrates. No prior hydrolysis or chemical modification of the sugars with a chromogenic reagent was required. Neutral oligosaccharides of progressively larger size were thus directly detectable with our method. The structures of compounds 4 and 5 are depicted below:

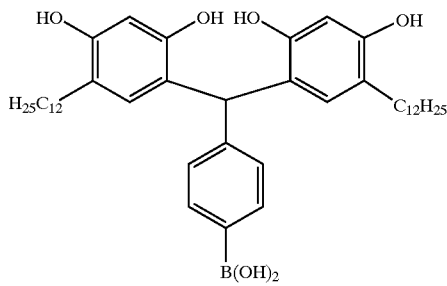

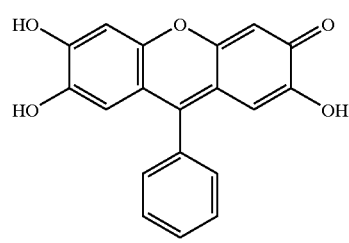

The novel color test for detecting oligosaccharides is simple to administer. In prototype studies, we have examined typical neutral oligomers composed entirely of glucose monomers, the malto-oligosaccharides. The malto-oligosaccharides (maltose through maltohexose), each at the same concentration of 4 mg in 2 mL, in the presence of compound 1, exhibited unprecedented absorbance responses in the visible region. The structure of compound 1 is depicted below:

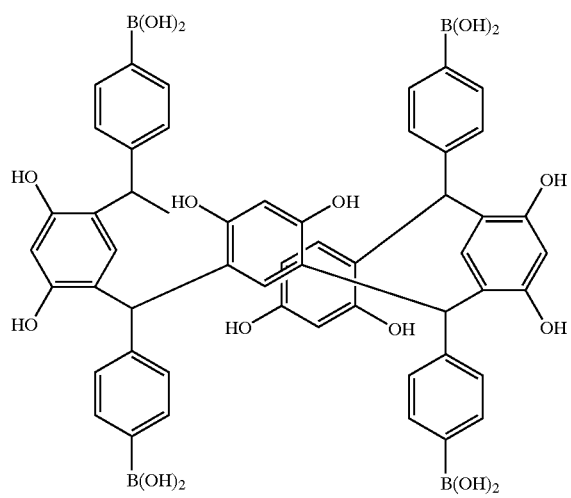

The novel methods use resorcinol condensation products (e.g., compounds 3, 4 and 6) or commercially available xanthene chromophores (e.g., compound 5) as colorimetric or fluorimetric sugar detection agents. Xanthene dyes (which include fluorescein, rose bengal, ethyl eosin, and others) are of great importance in photochemistry, photomedicine, photographic technology, tunable lasers, and fluorescence depolarization diagnostic devices. They have been used both as electron acceptors and as electron donors (to initiate free radical polymerizations), depending on the reactant. To the inventors' knowledge, there have been no prior reports of using xanthene compounds in saccharide-induced color changes. The structures of compounds 3, 4, 5 and 6 are depicted below:

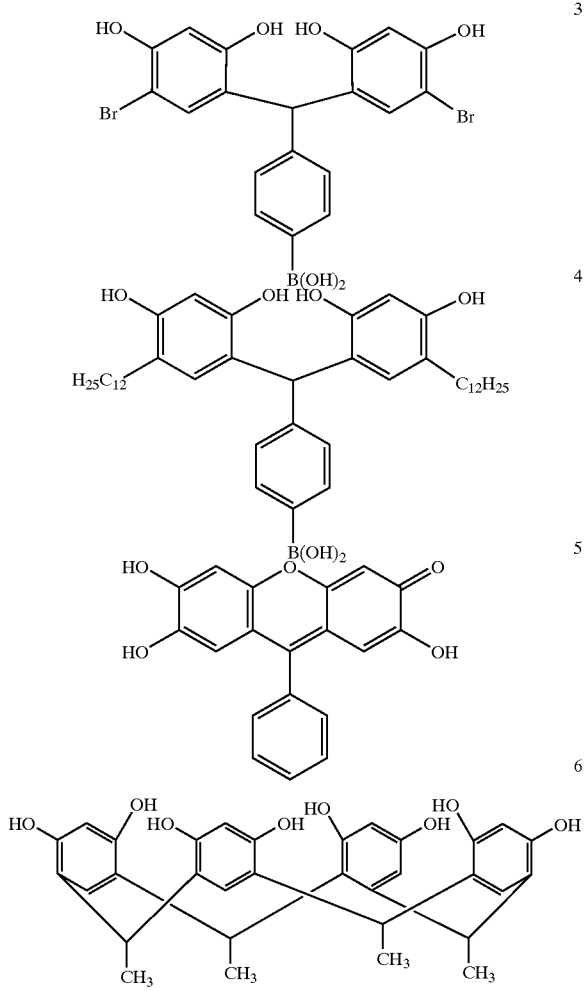

We have achieved several advances over the results previously reported by our research group and by others. We have now achieved the selective colorimetric detection of monosaccharides, at room temperature under neutral or near-neutral (preferably buffered) conditions. Color or fluorescence detection using compounds 3–6 is believed to be novel. Sugar color detection using resorcinarene or xanthene condensation products without boron has not been previously reported. Useful oligosaccharide color detection using mild reaction conditions is itself new. The new methods greatly simplify the color detection of mono- and oligosaccharides, without the need for corrosive reagents.

The compounds used in this invention generally are soluble in a water/aprotic polar solvent mixture, for example a mixed water/dimethylsulfoxide (DMSO) solvent. Other aprotic polar solvents that may be used such a mixture are well known in the art, and include, for example, tetrahydrofuran, dimethylformamide, sulfolane, acetonitrile, and hexamethylphosphoramide.

EXAMPLES 1 AND 2

Detection of Fructose

The syntheses of compounds 1 and 2 are described in P. Lewis et al. (1997). Colorless compound 1 or 2 (5.2 mM) was heated to a gentle reflux for 3 min in 0.9 mL DMSO to produce a colored solution. After cooling the solution to room temperature, we added fructose dissolved in 0.1 mL $H_2O$ at molar ratios of fructose:chemosensor ranging from 0 to 9. Even at these mM concentrations, the solution's color visibly changed from pink-purple to yellow upon addition of fructose. Spectrophotometric absorbance intensity changed notably as a function of fructose concentration at 535 nm and at 454 nm. The changes in absorbance were not linear, but were correlated with concentration. Absorbance at 454 nm increased with increasing fructose concentration, while absorbance at 535 nm decreased with increasing fructose concentration.

EXAMPLE 3

Selective Detection of Fructose in the Presence of a Large Excess of Glucose, and the Simultaneous Detection of Glucose in the Same Mixture Surprisingly, the detection of fructose as described in Examples 1 and 2 can be carried out in the presence of glucose, even in the presence of a very large molar excess of glucose. Addition of 1 equivalent of fructose to a solution containing compound 2 alone (previously heated, and then cooled to room temperature) produced a 29% increase in absorbance at 464 nm. The subsequent addition of 100 equivalents of glucose produced no perceptible change in absorbance at 464 nm. Then the further addition of another equivalent of fructose increased the absorbance at 464 nm by another 23%, demonstrating that absorbance at 464 nm had not been saturated. Rather, these results demonstrated that fructose concentrations could be measured at 464 nm with essentially no interference from glucose, even very high relative concentrations of glucose. The structure of compound 2 is depicted below:

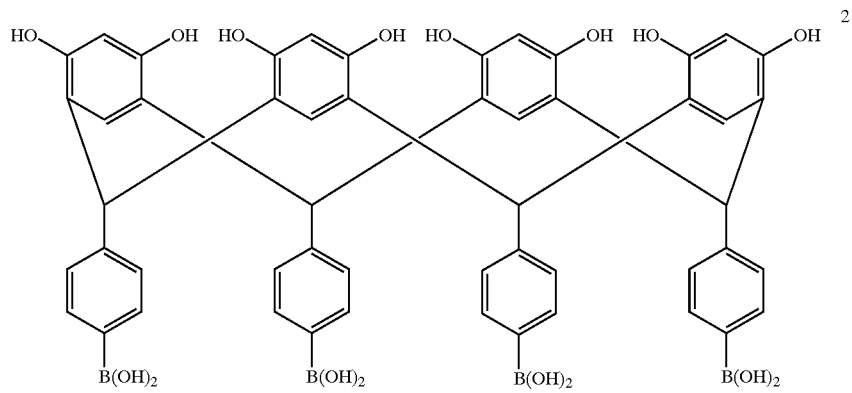

At 536 nm the absorbance of the solution containing compound 2 alone was lowered by 25% upon addition of 1 equivalent of fructose. The subsequent addition of 100 equivalents of glucose lowered the intensity an additional 8.3% (from A=0.746 to A=0.684). Then the further addition of another equivalent of fructose lowered the absorbance by 19% more.

Thus both fructose and glucose can be quantitated in a solution containing both monosaccharides, although the technique is more sensitive to fructose. First, absorbance measurements are made of a solution of compound 2 alone at both 464 nm and 536 nm. Then the test solution is mixed with the solution of compound 2, and absorbance is again measured at 464 nm and 536 nm. The change in absorbance at 464 nm depends on the fructose concentration alone, allowing the concentration of fructose to be determined. The measurement at 536 nm depends on both fructose and glucose concentrations; since the fructose concentration is known, the glucose concentration may be determined. Tables of absorbance at the two wavelengths as a function of saccharide concentration(s) using known standards may be made to assist in analyses.

EXAMPLES 4 AND 5

Selective Detection of Fructose in the Presence of Other Neutral Sugars

No significant changes in the absorbance spectra of colored solutions of fructose and preheated compound 2 (or compound 1) have been observed when other neutral carbohydrates are also present (besides glucose). For example, the absorbance spectrum of compound 2 plus 3 equivalents fructose was essentially unchanged when 3 equivalents of either sucrose or galactose were added. Similar results were observed upon adding α-lactose monohydrate, maltose monohydrate, and D-(+)-xylose.

EXAMPLES 6–15

Detection of Monosaccharides with Non-Boron-Containing Resorcinarene Compounds, or with Xanthene Dyes The synthesis of compound 6 is disclosed in A. Högberg, "Two stereoisomeric macrocyclic resorcinol-acetaldehyde condensation products," *J. Org. Chem.*, vol. 45, pp. 4498–4500 (1980). Separate colorless 5.2 mM solutions of compounds 3 and 6 were prepared by dissolving the compounds in a 9:1 (by volume) DMSO: $H_2O$ solvent mixture. To aliquots of these 5.2 mM solutions were added 3.0 equivalents of one of the following: D-(–)-fructose, α-D-glucose, sucrose, or different glucose phosphates. The mixtures were heated to a gentle reflux for 3 minutes, producing different solution colors, colors that were characteristic for each sugar tested. Table 1 presents monitored wavelengths λ, measured absorbances, and visually observed colors. Numerical values in Table 1 are the arithmetic means of three runs for each experiment. The results below for compound 6 indicated that the visual color sensing of saccharides is general for the resorcinarenes, including those without boronic acid groups. Compound 3 also produced a vivid, characteristic color for each sugar (generally different from the colors produced with compound 6).

TABLE 1

| | Compound 6 | | | Compound 3 | | |
|---|---|---|---|---|---|---|
| Sugar | λ (nm) | A | color | λ (nm) | A | color |
| none | 536 | 0.472 | purple | 532 | 0.807 | deep pink |
| sucrose | 536 | 0.329 | purple | 532 | 0.801 | deep pink |
| α-D-glucose | 536 | 0.172 | yellow-orange | 532 | 0.642 | bright peach |
| D-(–)-fructose | 536 | 0.128 | peach | 532 | 0.407 | deep yellow |
| α-D-glucose-1-phosphate disodium salt hydrate | 409 536 | 2.25 0.536 | orange-brown | 532 | 2.16 | bright reddish-orange |
| D-glucose-6-phosphate monosodium salt | 452 536 | 0.680 0.274 | yellow-brown | 532 | 1.73 | bright brownish-auburn |

EXAMPLES 16–18

Detection of Monosaccharides via Visible Region Fluorescence

Colorless $2.6 \times 10^{-5}$ M solutions of compound 3 were prepared by dissolving in a 9:1 (by volume) DMSO: $H_2O$ mixture heated for 8 min. To aliquots of these solutions were added different concentrations of one of the following sugars in $5.0 \times 10^{-2}$ M $K_2CO_3$ buffer: D-(–)-fructose, α-D-glucose, or D-(+)-galactose. Fluorescence intensities of the solutions were then measured using excitation at 533 nm and emission at 550 nm. We then derived correlation plots of fluorescence intensity versus sugar concentration (not shown). We observed a steady (nearly linear) decrease in fluorescence intensity as saccharide concentration increased. Compound 3 allows fluorescence monitoring of mM levels of glucose, fructose and galactose, in ranges of concentrations typically found in blood.

EXAMPLES 19 AND 20

Detection of Fructose in the Presence of Glucose, and Vice Versa

Colorless $5.2 \times 10^{-5}$ M solutions of compound 3 were prepared by dissolving in a 9:1 (by volume) DMSO:$H_2O$ mixture heated for 8 min. To aliquots of these solutions were added different concentrations of α-D-glucose in the presence of a fixed concentration ($5.2 \times 10^{-5}$ M) of D-(–)-fructose; or were added different concentrations of D-(–)-fructose in the presence of a fixed concentration ($5.2 \times 10^{-5}$ M) of α-D-glucose. In each case, fluorescence intensities of the solutions were then measured using excitation at 533 nm and emission at 552 nm. We then prepared correlation plots of fluorescence intensity versus sugar concentration (not shown).

We observed a steady (nearly linear) decrease in fluorescence intensity as the concentration of either glucose or fructose increased in the mM range in the presence of a fixed concentration of the other, although the slopes and intercepts of the two plots differed. The slope for the fructose binding decreased approximately twice as rapidly as that for glucose, indicating that compound 3 is more sensitive to fructose than to glucose.

EXAMPLE 21

Absorbance Intensity of Compound 3 with Glucose as a Nearly Linear Function of Glucose Concentration Mixtures of compound 3 ($5.2 \times 10^{-5}$ M) with glucose at various concentrations in the mM range produced an absorbance at 520 nm that decreased (nearly linearly) as the glucose concentration increased (data not shown).

EXAMPLE 22

Absorbance Spectrum of Compound 5 Mixed with Different Saccharides

Following gentle reflux with any one of three different saccharides, commercially available xanthene dye compound 5 (commercially available from Aldrich, Milwaukee, Wis.) exhibited significant colorimetric responses to the reducing sugars glucose and fructose, but essentially no change in spectrum with the non-reducing sugar sucrose. In addition, other non-reducing sugars, such as methyl gluco- and methyl galactopyranoside, exhibited only minor spectral changes when heated with compound 5. Thus a reducing sugar may be monitored via solution color changes and absorbance spectral changes that follow heating the dye in the presence of non-reducing sugars.

EXAMPLE 23

General Method for Determination of Sialic Acid Using Compound 3

The most naturally abundant sialic acid, N-acetylneuraminic acid, was dissolved in buffer (aqueous HEPES, pH adjusted to 7.5) in various mM concentrations. Each of the solutions was added at room temperature to a DMSO solution of compound 3 (5.2 mM). Sialic acid concentration was monitored by observing changes in absorbance at 531 nm and 476 nm, along with a concomitant solution color change from pink-purple to yellow. Absorbance increased with increasing sialic acid concentration at 476 nm, and decreased with increasing sialic acid concentration at 531 nm. The absorbance intensity exhibited a nearly linear dependence on sialic acid concentration at 531 nm (data not shown).

EXAMPLE 24

Selective Detection of Sialic Acid in the Presence of Neutral Sugars

No significant change was observed in the absorbance spectrum of a colored solution of the sialic acid N-acetylneuraminic acid and compound 3 when other neutral carbohydrates were present. For example, adding 3 equivalents of either fructose or fucose to the system otherwise described in Example 23 did not cause significant changes in the absorbance spectrum of the mixture between 320 nm and 700 nm; and in particular did not cause significant changes at the 531 nm peak absorption wavelength. By contrast, added fructose or fucose is known to interfere with prior sialic acid color tests that use harsher reaction conditions.

EXAMPLE 25

Detection of Sialic Acid with Commercial Xanthene Dye 5

Xanthene compound 5 allowed micromolar levels of sialic acid to be detected both by visual inspection and spectrophotometrically. A 10 $\mu$M solution of compound 5 was prepared in a 9:1 DMSO:water mixture. When this compound 5 solution was mixed with a HEPES-buffered (pH 7.5) sialic acid solution in water at room temperature, we observed a nearly instantaneous color change from pink to yellow. Absorbance spectra measured at different concentrations of sialic acid showed that the absorbance intensity increased at 476 nm, and decreased at 531 nm (data not shown).

EXAMPLES 26–29

Color Detection of Oligosaccharides with Compound 1

No known prior detection method allows for the efficient direct visible monitoring of neutral oligosaccharides larger than a trisaccharide. The present invention overcomes this prior limitation. A prototype demonstration was conducted with the malto-oligosaccharides from maltotriose to malto-hexaose. In separate experiments, an equal mass (4 mg) of each of these malto-oligosaccharides was heated in the presence of 10 mg of compound 1 to a gentle reflux for 3 min in 9:1 (by volume) DMSO:H$_2$O (2 mL). The solutions each visibly changed color, and the absorbance responses were read from a spectrophotometer (data not shown). As the number of glucose subunits per oligosaccharide increased, the absorbance intensities at visible wavelengths also increased as compared to that for compound 1 alone. The solution colors were deep orange yellow, yellow-gold, pale orange, orange, purple, and peach for the series maltose through maltoheptaose, respectively. Similar results were also seen following the substitution of compound 2 for compound 1.

EXAMPLES 30–34

Color Detection of Oligosaccharides with Compound 4

Although the absorbance of compound 4 strongly reacts to the presence of saccharides, it does not distinguish well between monosaccharide and oligosaccharide, or between different oligosaccharides. This lack of selectivity is highly desirable in certain applications, for example, in detection of carbohydrates eluting from an HPLC column. compound 4 (520 $\mu$M in 9:1 DMSO:H$_2$O, 2 mL) was heated for 2 min. to 120° C., either alone, or in the presence of 4 mg of one of the following species: maltose, maltotriose, maltotetraose, maltopentaose, or maltohexaose. While the spectra of compound 4 with saccharides were clearly different from the spectrum of compound 4 alone, the spectra with the various saccharides were all very similar to one another (data not shown). These results demonstrated the direct visible detection of typical neutral oligosaccharides derived from glucose, without a significant decrease in absorbance intensity for the higher oligosaccharides (at the same mass concentration). Decreases in absorbance were particularly pronounced at 535 nm. Qualitatively, the solution colors changed from pink for heated compound 4 alone to light orange for the heated mixture of compound 4 with a saccharide.

EXAMPLES 35–39

Color Detection of Oligosaccharides with Compound 5

Similarly, the absorbance of compound 5 strongly reacts to the presence of saccharides, but does not distinguish well between monosaccharide and oligosaccharide, or between different oligosaccharides. Compound 5 (3 $\mu$M in 9:1 DMSO:H$_2$O, 2 mL) was heated for 2 min. to 120° C., either alone, or in the presence of 4 mg of one of the following species: maltose, maltotriose, maltotetrose, maltopentaose, or maltohexaose. While the spectra of compound 5 with saccharides were clearly different from the spectrum of compound 5 alone, the spectra with the various saccharides were all very similar to one another (data not shown). These results demonstrated the direct visible detection of typical neutral oligosaccharides derived from glucose, without a significant decrease in absorbance intensity for the higher oligosaccharides (at the same mass concentration). Decreases in absorbance were particularly pronounced at 535 nm. Qualitatively, the solution colors changed from pink for heated compound 5 alone to light orange for the heated mixture of compound 5 with a saccharide.

EXAMPLE 40

Synthesis of Compound 3

In a 300 mL three-necked, round bottom flask at room temperature, we placed 4-bromoresorcinol (2.00 g, 10.6 mmol), 4-formylphenylboronic acid (0.793 g, 5.29 mmol), and ethanol (30 mL), and stirred until clear. Concentrated HCl (15 mL) was then added dropwise to the reaction mixture with stirring. The mixture was then heated in a sand bath to 70° C. under $N_2$ for 3 hours. After cooling to room temperature, the mixture was neutralized with sodium bicarbonate, and refluxed with decolorizing carbon to remove the solution color. The product was filtered, recrystallized from methanol, again filtered, and the precipitate was dried. Compound 3 was recovered (1.64 g, 61%). m.p. >300° C.; $^1$H NMR (400 MHz, DMSO-$d_6$) δ 5.70 (s, 1H), 6.50 (s, 2H), 6.53 (s, 2H), 6.91 (d, J=8.0 Hz, 2H), 7.96(bs, 2H), 9.92 (s, 2H); $^{13}$C NMR (100 MHz, DMSO-$d_6$) δ 41.9, 97.5, 103.6, 123.2, 127.9, 131.6, 132.4, 134.0, 145.7, 152.8, 155.0; uv $\lambda_{max}$ 286 nm, (DMSO); MALDI MS m/z calculated 509.94, found 510.77 ($M^+$).

EXAMPLE 41

Synthesis of Compound 4

In a 300 mL three-necked, round bottom flask at room temperature, we placed 4-dodecylresorcinol (3.00 g, 10.8 mmol), 4-formylphenylboronic acid (0.808 g, 5.39 mmol), and ethanol (30 mL), and stirred until clear. Concentrated HCl (15 mL) was then added dropwise to the reaction mixture with stirring. The mixture was then heated in a sand bath to 70° C. under $N_2$ for 3 hours. After cooling to room temperature, the mixture was neutralized with sodium bicarbonate and filtered. Ethanol was then removed in vacuo. The compound was then extracted into ethyl acetate, and the solvent was again removed in vacuo. The compound was purified by a solid-liquid extraction using $CH_2Cl_2$. After filtration compound 4 was recovered (1.27 g, 34%) as a light-brown solid. m.p. >300° C.; $^1$H NMR (250 MHz, DMSO-$d_6$) δ 1.31 (m, 46H), 2.25–2.29 (m, 4H), 5.83 (s, 1H), 6.29 (s, 2H), 6.36 (s, 2H), 6.89 (d, J=7.8 Hz, 2H), 7.61 (d, J=7.9 Hz, 2H), 7.84 (bs, 2H), 8.74 (s, 2H), 8.78 (s, 2H); $^{13}$C NMR (250 MHz, DMSO-$d_6$) δ 14.8, 23.0, 29.6, 29.7, 30.0, 30.1, 30.5, 32.2, 103.1, 118.1, 121.5, 128.7, 131.8, 134.4, 149.1, 154.1; uv $\lambda_{max}$ 286 nm, (DMSO/$H_2O$); MALDI MS m/z (anthracene matrix) calculated for $C_{43}H_{65}BO_6$ 688.7, found 688.7 ($M^+$), $v_{max}$/cm$^{-1}$ (OH) 3461, ($CH_2$) 2925, (CH) 2854, (aromatic C=C) 1657, 1521, (COH) 1055, 1027, 1008.

Extension to Other Compounds

The specific compounds used in the above Examples are not, of course the only compounds that may be used in practicing the present invention. Modifications of the basic structures may also be used. For example, anywhere compound 1 may be used, one may substitute compound 7:

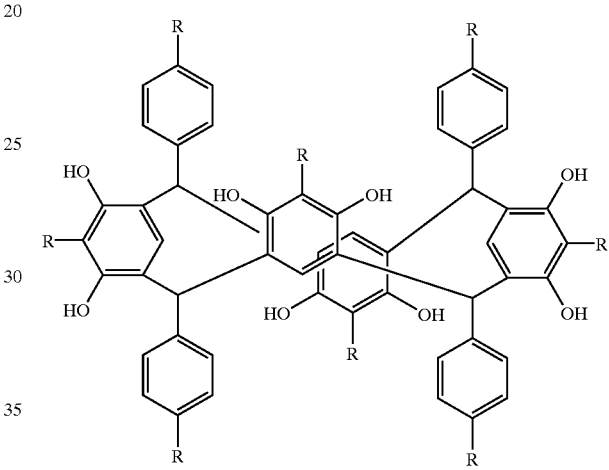

7 wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different.

Likewise, anywhere compound 2 or compound 6 may be used, one may substitute compound 8:

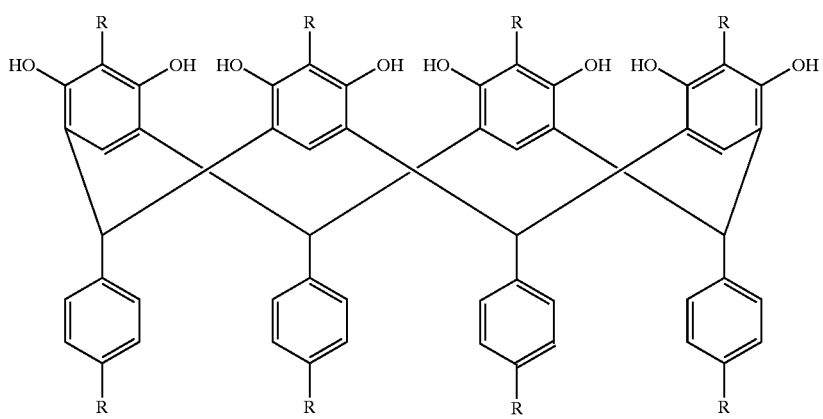

8 wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different.

Anywhere compound 3 or compound 4 may be used, one may substitute compound 9:

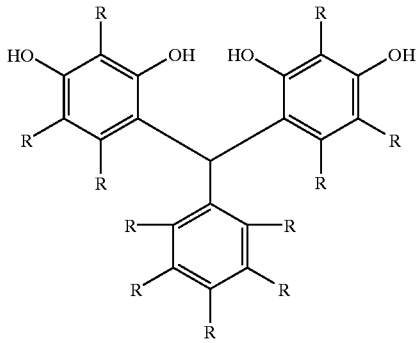

9 wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different.

Anywhere compound 5 may be used, one may substitute compound 10:

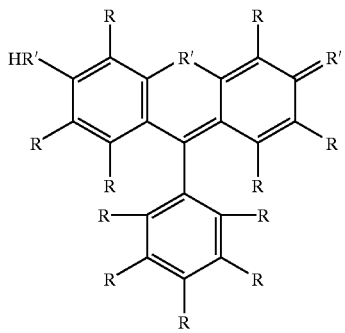

10 wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein R'=C, N, O, or S, and wherein the different R's may be the same or different.

Miscellaneous

As used in the specification and claims, to hold a compound at a temperature and for a time sufficient to induce a color in the compound usually, but not always, implies heating of the compound prior to its use. Once a color has thus been induced, that color is usually stable for a period of hours, days, or even longer, even after the source of heat has been removed. Some compounds, for example compound 5, do not require heating above ambient temperature for induction of color. In such a case, to hold the compound at a temperature and for a time sufficient to induce a color in the compound may require nothing more than maintaining the compound at a temperature at which color is present; a heating step may not be required in such a case.

The complete disclosures of all references cited in this specification are hereby incorporated by reference. Also incorporated by reference is the full disclosure of the following paper, which is not prior art to this application: P. Lewis et al., "Visual Sensing of Saccharides Promoted by Resorcinol Condensation Products," *Organic Letters*, vol. 2, pp. 589–592 (2000). Also incorporated by reference is the full disclosure of the following manuscript (including its figures): R. Strongin, "Biomolecule Color Sensing," unpublished manuscript (2000). In the event of an otherwise irreconcilable conflict, however, the present specification shall control.

We claim:

1. A method for selectively detecting fructose in a sample, wherein one or more sugars other than fructose are present in the sample, said method comprising the steps of:

(a) preparing a solution, in a mixed water/aprotic polar solvent, of at least a portion of the sample and a compound selected from the group consisting of compounds having structure 7 or having structure 8 as follows:

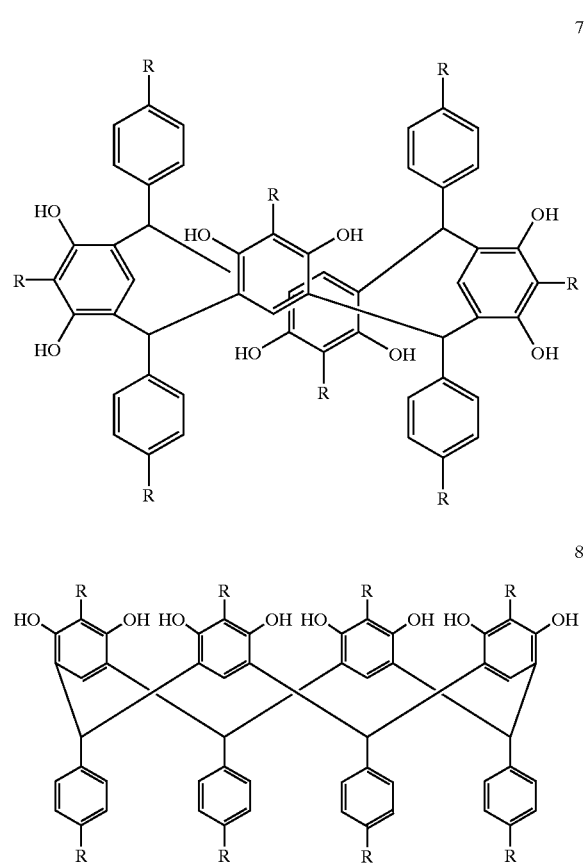

wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein said compound has previously been held at a temperature and for a time sufficient to induce a color in said compound; and (b) measuring the absorbance or fluorescence of the solution at a visible or ultraviolet wavelength or wavelengths at which the absorbance or fluorescence is a function of the fructose concentration.

2. A method as recited in claim 1, wherein said method is conducted at ambient temperature.

3. A method as recited in claim 1, wherein said compound is compound 1:

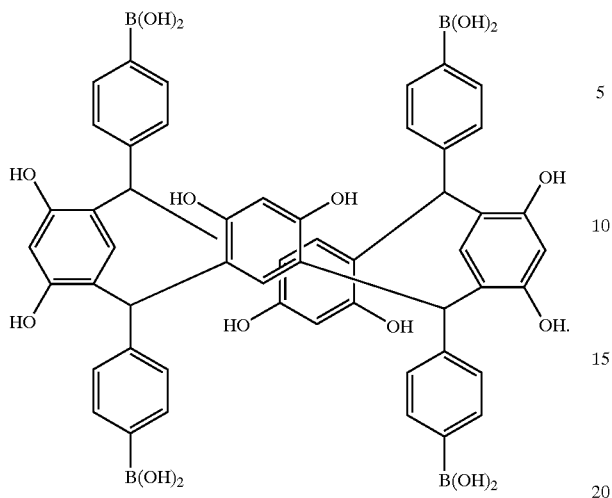

4. A method as recited in claim 1, wherein said compound is compound 2:

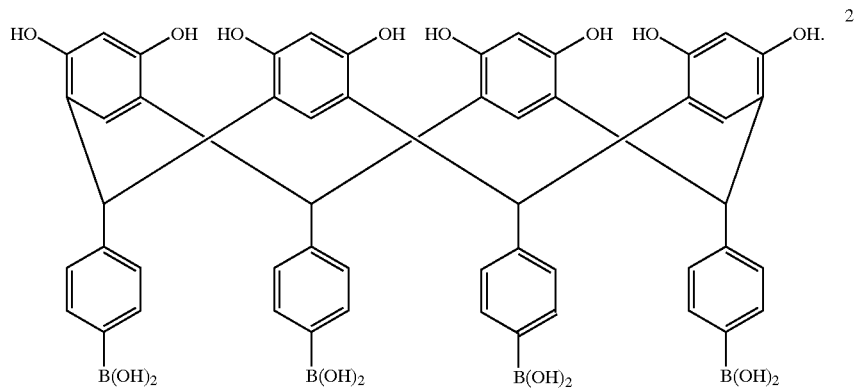

5. A method for selectively detecting glucose in a sample, wherein one or more sugars other than glucose are present in the sample, said method comprising the steps of:

(a) preparing a solution, in a mixed water/aprotic polar solvent, of at least a portion of the sample and a compound selected from the group consisting of compounds having structure 7 or having structure 8 as follows:

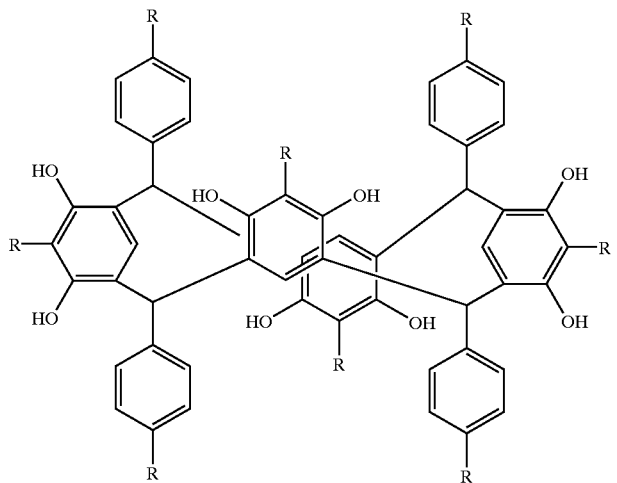

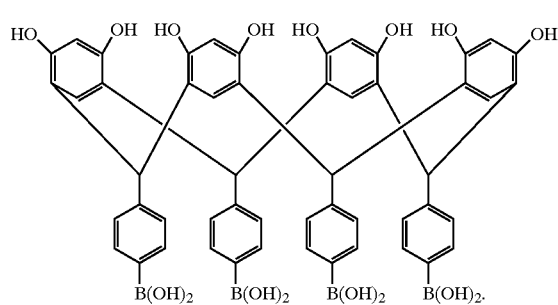

wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein said compound has previously been held at a temperature and for a time sufficient to induce a color in said compound; and (b) measuring the absorbance or fluorescence of the solution at a visible or ultraviolet wavelength or wavelengths at which the absorbance or fluorescence is a function of the glucose concentration.

6. A method as recited in claim 5, wherein said method is conducted at ambient temperature.

7. A method as recited in claim 5, wherein said compound is compound 1:

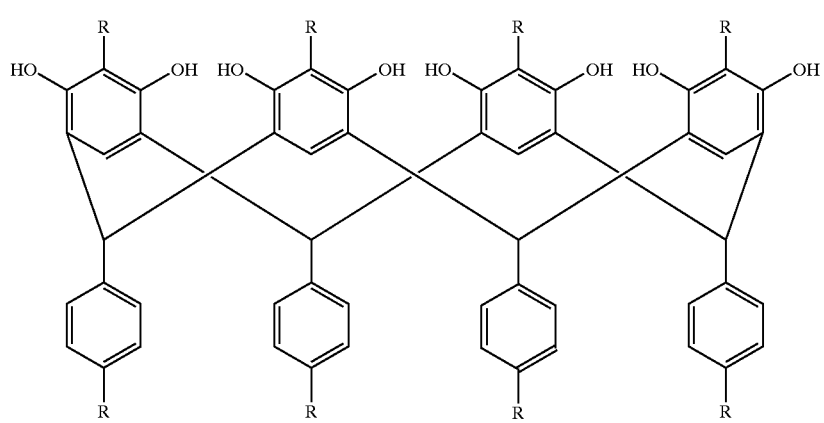

8. A method as recited in claim 5, wherein said compound is compound 2:

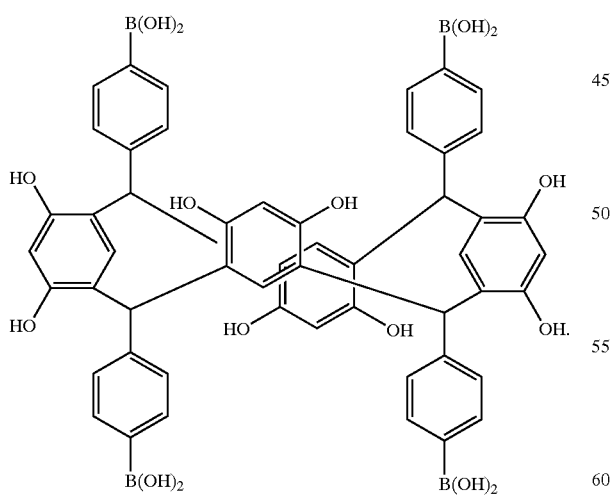

9. A method for selectively detecting fructose in a sample that also contains glucose, wherein sugars other than fructose and glucose may be present or absent from the sample, said method comprising the steps of:

(a) preparing a solution, in a mixed water/aprotic polar solvent, of at least a portion of the sample and a compound selected from the group consisting of compounds having structure 7 or having structure 8 as follows:

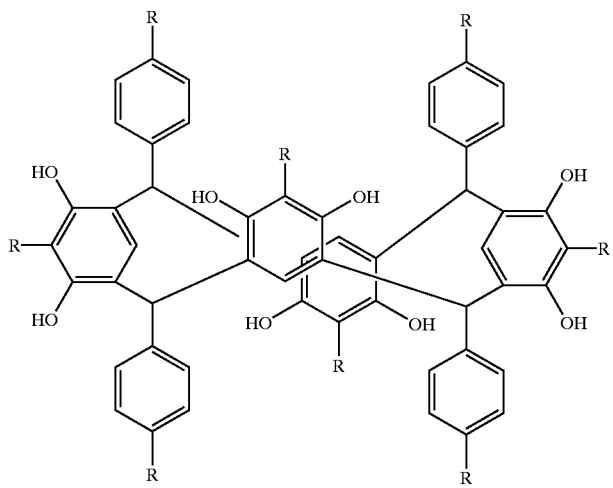

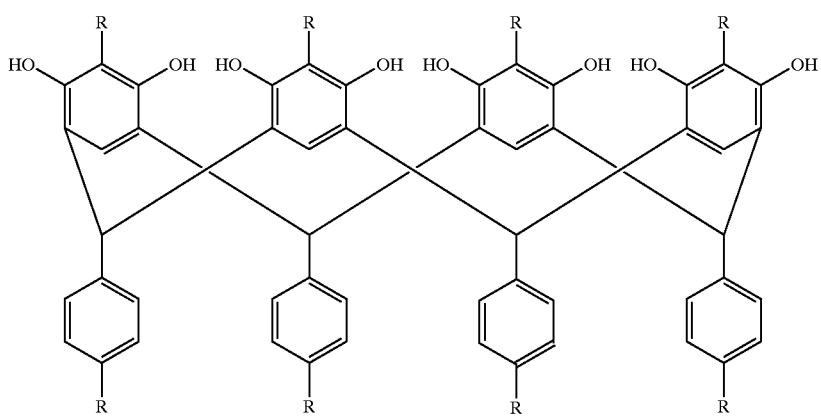

wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein said compound has previously been held at a temperature and for a time sufficient to induce a color in said compound; and (b) measuring the absorbance or fluorescence of the solution at a visible or ultraviolet wavelength or wavelengths at which the absorbance or fluorescence is a function of the fructose concentration.

10. A method as recited in claim 9, wherein said method is conducted at ambient temperature.

11. A method as recited in claim 9, wherein said compound is compound 1:

12. A method as recited in claim 9, wherein said compound is compound 2:

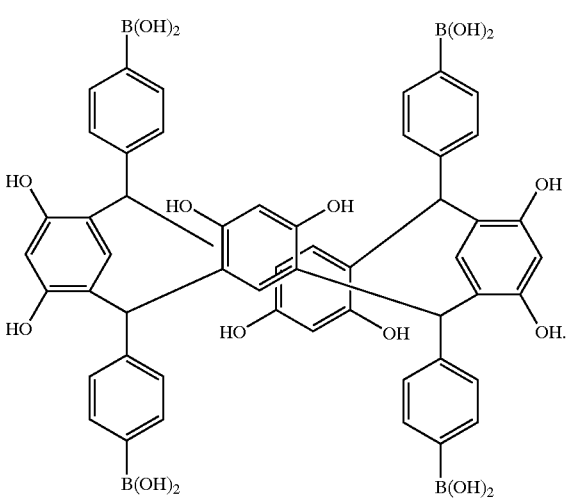

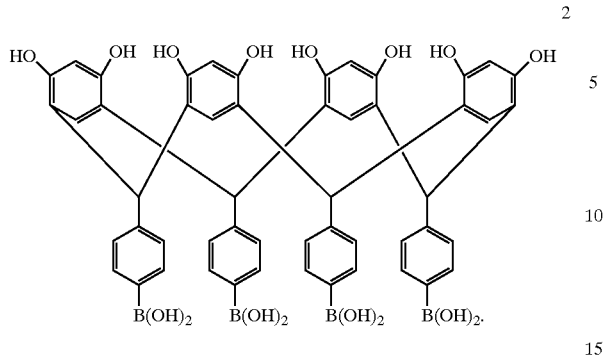

2

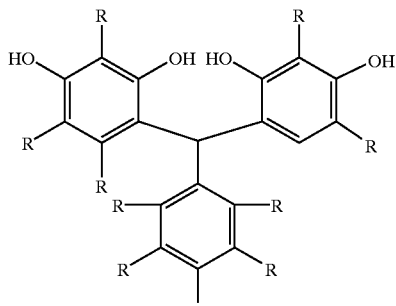

9

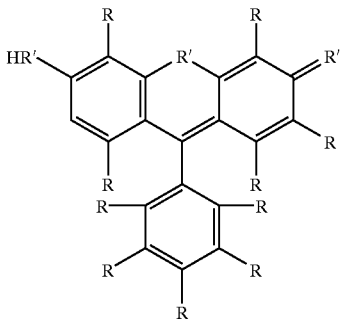

10

13. A method for selectively detecting sialic acid in a sample, wherein one or more carbohydrates other than sialic acid are present in the sample, said method comprising the steps of:

(a) preparing a solution, in a mixed water/aprotic polar solvent, of at least a portion of the sample and a compound selected from the group consisting of compounds having structure 7, structure 8, structure 9, or structure 10 as follows:

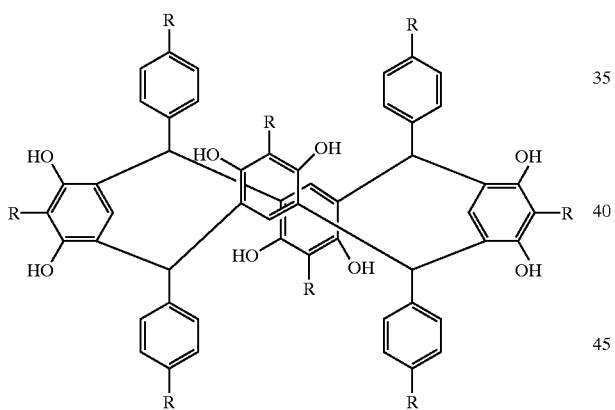

7

8 wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein R'=C, N, O, or S, and wherein the different R's may be the same or different;

wherein said compound has previously been held at a temperature and for a time sufficient to induce a color in said compound; and (b) measuring the absorbance or fluorescence of the solution at a visible or ultraviolet wavelength or wavelengths at which the absorbance or fluorescence is a function of the sialic acid concentration.

14. A method as recited in claim 13, wherein the solution comprises a buffered solution of approximately neutral pH.

15. A method as recited in claim 13, wherein said method is conducted at ambient temperature.

16. A method as recited in claim 13, wherein said compound is compound 3:

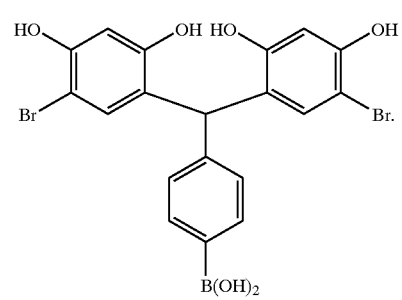

3

17. A method as recited in claim 13, wherein said compound is compound 5:

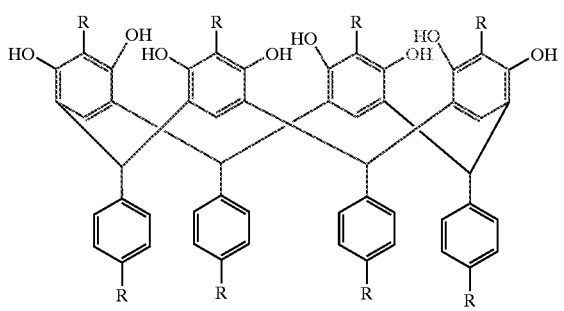

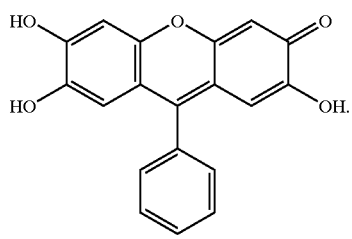

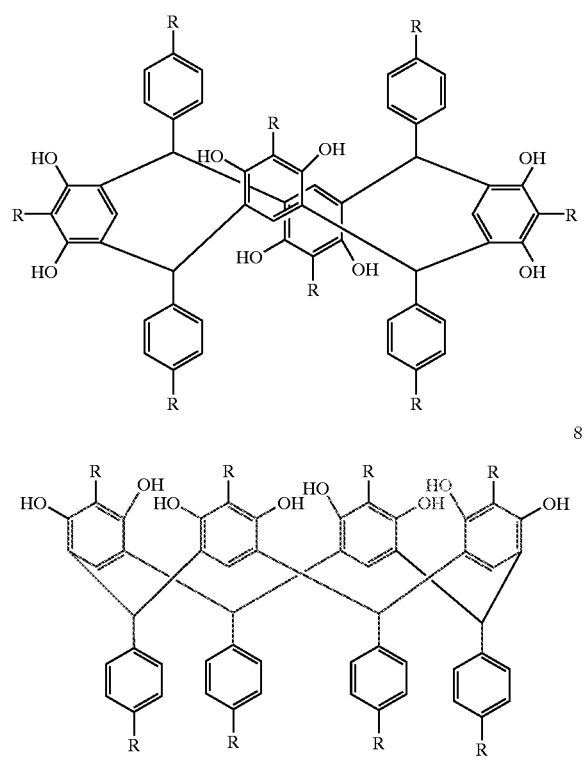

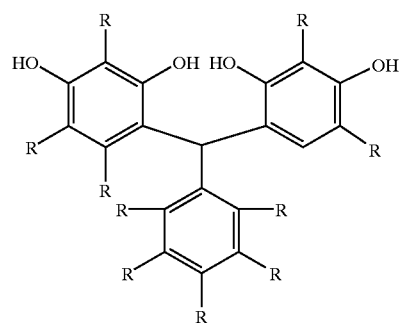

18. A method for non-specifically detecting oligosaccharides in a sample, said method comprising the steps of:

(a) preparing a solution, in a mixed water/aprotic polar solvent, of at least a portion of the sample and a compound selected from the group selected from the group consisting of compounds having structure 7, structure 8, structure 9, or structure 10 as follows:

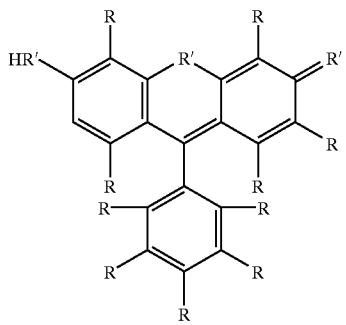

wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein R'=C, N, O, or S, and wherein the different R's may be the same or different;

wherein said compound has previously been held at a temperature and for a time sufficient to induce a color in said compound; and (b) measuring the absorbance or fluorescence of the solution at a visible or ultraviolet wavelength or wavelengths at which the absorbance or fluorescence is a function of oligosaccharide concentration.

19. A method as recited in claim 18, wherein said compound is compound 1:

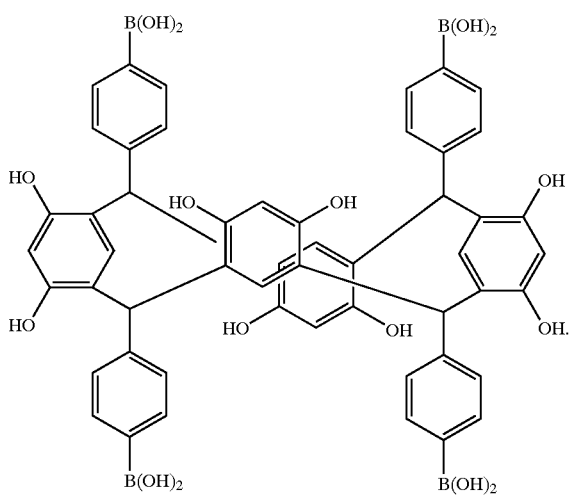

20. A method as recited in claim 18, wherein said compound is compound 4:

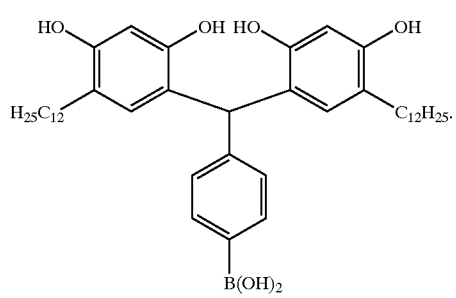

21. A method as recited in claim 18, wherein said compound is compound 5:

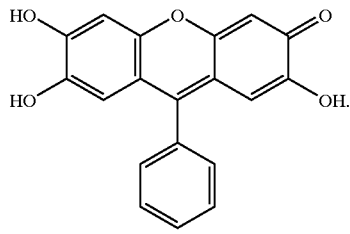

22. A method for detecting monosaccharides in a sample, said method comprising the steps of:
   (a) preparing a solution, in a mixed water/aprotic polar solvent, of at least a portion of the sample and a compound selected from the group selected from the group consisting of compounds having structure 9 or structure 10 as follows:

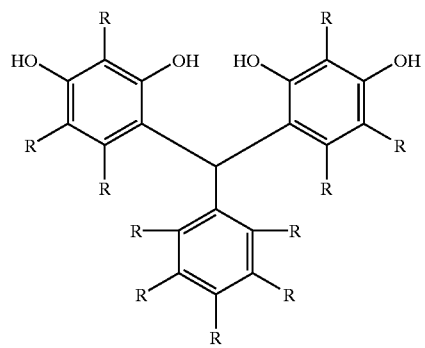

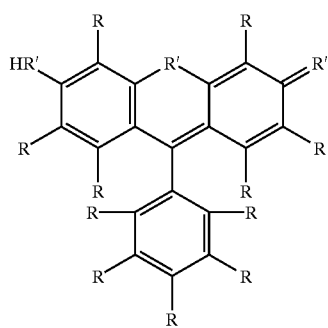

wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different; and wherein R'=C, N, O, or S, and wherein the different R's may be the same or different;
   wherein said compound has previously been held at a temperature and for a time sufficient to induce a color in said compound; and
   (b) measuring the absorbance or fluorescence of the solution at a visible or ultraviolet wavelength or wavelengths at which the absorbance or fluorescence is a function of monosaccharide concentration.

23. A method as recited in claim 22, wherein said compound is compound 3:

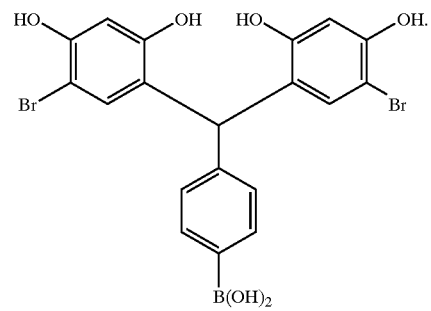

24. A method as recited in claim 22, wherein said compound is compound 4:

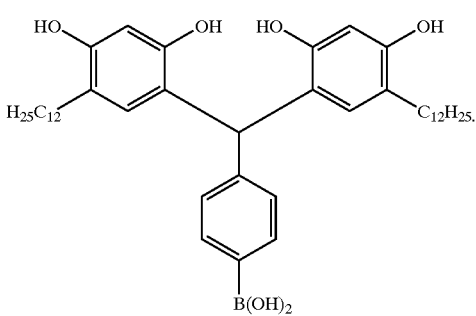

25. A method as recited in claim 22, wherein said compound is compound 5:

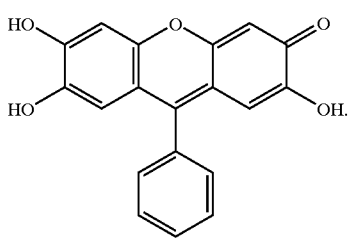

26. A compound having the structure 9 as follows:

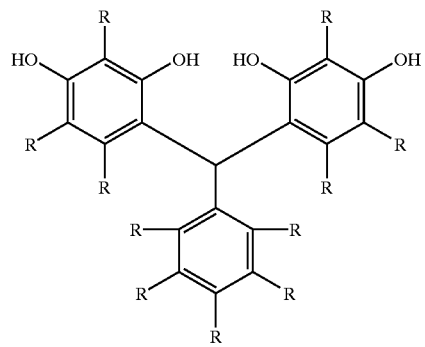

wherein R=H, $C_1$–$C_4$ alkyl, halogen, thio, hydroxy, $C_1$–$C_4$ ether, $C_1$–$C_4$ carbonyl, $C_0$–$C_4$ amino, $C_0$–$C_4$ amido, $C_1$–$C_4$ ester, aryl, boronic acid, or metal, and wherein the different Rs may be the same or different.
27. A compound as recited in claim 26, wherein said compound has the structure 3 as follows:
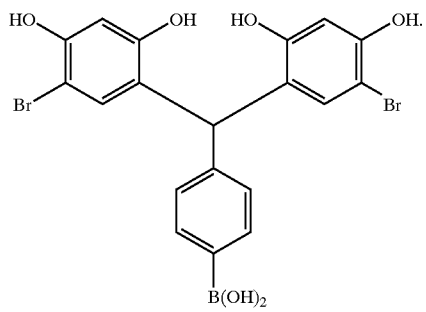
28. A compound as recited in claim 26, wherein said compound has structure 4 as follows:
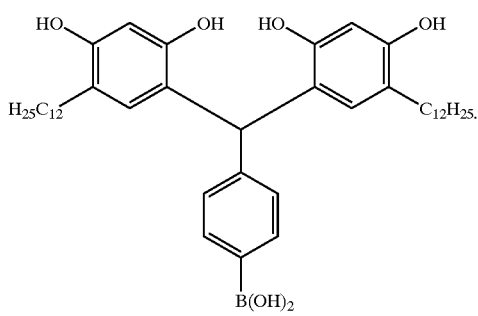
* * * * *